US008421854B2

(12) United States Patent  (10) Patent No.: US 8,421,854 B2
Zerkin  (45) Date of Patent: Apr. 16, 2013

(54) SYSTEM AND METHOD FOR MOTION CAPTURE

(76) Inventor: Noah Zerkin, Brooklyn, NY (US)

(*) Notice: Subject to any disclaimer, the term of this patent is extended or adjusted under 35 U.S.C. 154(b) by 726 days.

(21) Appl. No.: 12/509,248

(22) Filed: Jul. 24, 2009

(65) Prior Publication Data

US 2010/0110169 A1      May 6, 2010

Related U.S. Application Data

(60) Provisional application No. 61/083,379, filed on Jul. 24, 2008, provisional application No. 61/204,416, filed on Jan. 6, 2009.

(51) Int. Cl.
*A61B 1/06*       (2006.01)
(52) U.S. Cl.
USPC .............................................. 348/77; 600/595
(58) Field of Classification Search .................... 348/77; 600/595
See application file for complete search history.

(56) References Cited

U.S. PATENT DOCUMENTS

| 4,308,584 | A * | 12/1981 | Arai .............................. 700/249 |
| 6,895,305 | B2 | 5/2005 | Lathan et al. |
| 7,862,522 | B1 * | 1/2011 | Barclay et al. ................. 600/595 |
| 2004/0133249 | A1 | 7/2004 | Gesotti |
| 2005/0134716 | A1 | 6/2005 | Vice |
| 2005/0257175 | A1 | 11/2005 | Brisben et al. |
| 2006/0130594 | A1 * | 6/2006 | Ikeuchi ....................... 73/862.08 |
| 2007/0032748 | A1 * | 2/2007 | McNeil et al. ................ 600/595 |
| 2007/0179560 | A1 * | 8/2007 | Tong et al. ...................... 607/48 |
| 2008/0010890 | A1 | 1/2008 | Vice et al. |
| 2009/0204031 | A1 * | 8/2009 | McNames et al. ............ 600/595 |
| 2009/0322680 | A1 * | 12/2009 | Festa .............................. 345/160 |
| 2009/0322763 | A1 * | 12/2009 | Bang et al. ..................... 345/474 |
| 2010/0023314 | A1 * | 1/2010 | Hernandez-Rebollar ......... 704/3 |
| 2010/0249637 | A1 * | 9/2010 | Walter et al. .................. 600/544 |

OTHER PUBLICATIONS

Using an Accelerometer Sensor to Measure Human Hand Motion by Brian Barkley Graham dated May 11, 2000.

* cited by examiner

*Primary Examiner* — Tammy Nguyen
*Assistant Examiner* — Jonathan Bui
(74) *Attorney, Agent, or Firm* — Sofer & Haroun, LLP

(57) ABSTRACT

A motion capture device provided for capturing motion of a limb having two sections, connected by a flexing joint. A sensor array is mounted to a first section of a limb, having at least one gyroscopic sensor element and at least one accelerometer. A sensor for attachment across the flexible joint is coupled to the sensor array and extends away from the sensor array across the flexing joint to a second section of the limb, where the location and motion of the limb is captured by a combination of data obtained from the at least one gyroscopic sensor element and at least one accelerometer of the sensor array and the sensor for said flexible joint.

15 Claims, 7 Drawing Sheets

SYSTEM AND METHOD FOR MOTION CAPTURE

RELATED APPLICATIONS

This application claims the benefit of priority from U.S. Provisional Patent Application No. 61/083,379, filed on Jul. 24, 2008 and U.S. Provisional Patent Application No. 61/204, 416, filed on Jan. 6, 2009 both of which are incorporated by reference.

BACKGROUND

1. Field of the Invention

This application relates to motion capture. More particularly, this application relates to a motion capture system and method for tracking the motion of limbs.

2. Description of Related Art

Motion capture devices are available in a variety of formats and are used for, among other things, tracking the motion of one or more limbs of a wearer. Such devices may be used in a variety of manners, including video/entertainment, medical/rehabilitation, device or remote device actuation, etc. . . .

There are currently three main types of motion capture systems on the market. These are optical, inertial, and deformation-detecting type motion capture devices.

The first type of system is an optical motion capture device. These optical devices use one or more arrays of high-resolution cameras arranged around a stage on which action can take place. In most incarnations of such optical systems, the subjects are required to don suits studded in semi-reflective orbs about the size of table-tennis balls. The most prominent of these optical systems, and the current overall market leader, is that developed and sold by Vicon™.

A second type of motion capture system is the inertial system. These inertial system use inertial measurement units mounted to each limb segment and extremity of the subject. These units utilize a combination of accelerometric, magnetometric, and gyroscopic sensors that data from which is used to record the movement of the limbs, to which they are attached, in three-dimensional space. Such systems allow for limb tracking with a high degree of precision. Currently, the inertial system sold under the name Moven™ is probably the most recognized of these systems.

The third type of motion capture system uses deformation-detecting fiber optic strands embedded in flexible ribbons. The most notable example of this technique is probably the ShapeWrap II™ system by Measurand Systems™/Inition™.

Of the available motion capture systems, the Vicon™ optical type motion capture system is recognized to be the most accurate motion capture system, but is very limited in use. For example, such as system is limited to use within a limited area defined by the perimeter of cameras, and requires significant time to get subjects in and out of the suits they must wear. Such systems are also very expensive, both in the initial outlay for equipment, and in the expertise required for its use and maintenance.

The Moven™ inertial type motion capture system, owing to its intensive use of sensors, is both expensive, and also requires the use of a suit. Similarly, the ShapeWrap™ deformation-detecting motion capture technology from Measurand™ is also somewhat cumbersome and expensive.

In each case, the existing motion capture devices focus on professional and institutional markets, and the prices reflect this.

OBJECTS AND SUMMARY

The present arrangement overcomes the drawbacks associated with prior art motion capture systems and methods by providing a lower cost inertial motion capture system that employs a more simple and effective design.

In one arrangement, an inertial type sensor is employed that utilizes a single primary sensor array having accelerometric and gyroscopic sensors. Such a sensor array is located on only one segment of a limb such as a lower arm segment. From the primary sensor array, another sensor extends outward to the other segment of the limb across the flexible joint, such as an upper arm segment. The combination of accelerometric and gyroscopic sensors on a first limb segment with a flexible sensor that extends to the adjacent limb segment achieves desirable motion detection results with only one primary sensor array, the primary sensor array employing lower cost sensor components.

In another arrangement of the invention, a series of calculations are made using the data input from the accelerometric, gyroscopic and flexible sensor components to calculate the location of the tracked limb.

To this end, the present arrangement provides for a motion capture device for capturing motion of a limb having two sections, connected by a flexing joint. The device includes a sensor array mounted to a first section of a limb having at least one gyroscopic sensor element and at least one accelerometer. Another sensor for attaching across the flexible joint is coupled to the sensor array and extends away from the sensor array across a flexing joint to a second section of the limb. The location and motion of the limb is captured by a combination of data obtained from the at least one gyroscopic sensor element and at least one accelerometer of the sensor array and the sensor for the flexible joint.

BRIEF DESCRIPTION OF THE DRAWINGS

The present invention can be best understood through the following description and accompanying drawings, wherein.

DETAILED DESCRIPTION

Figure 1:
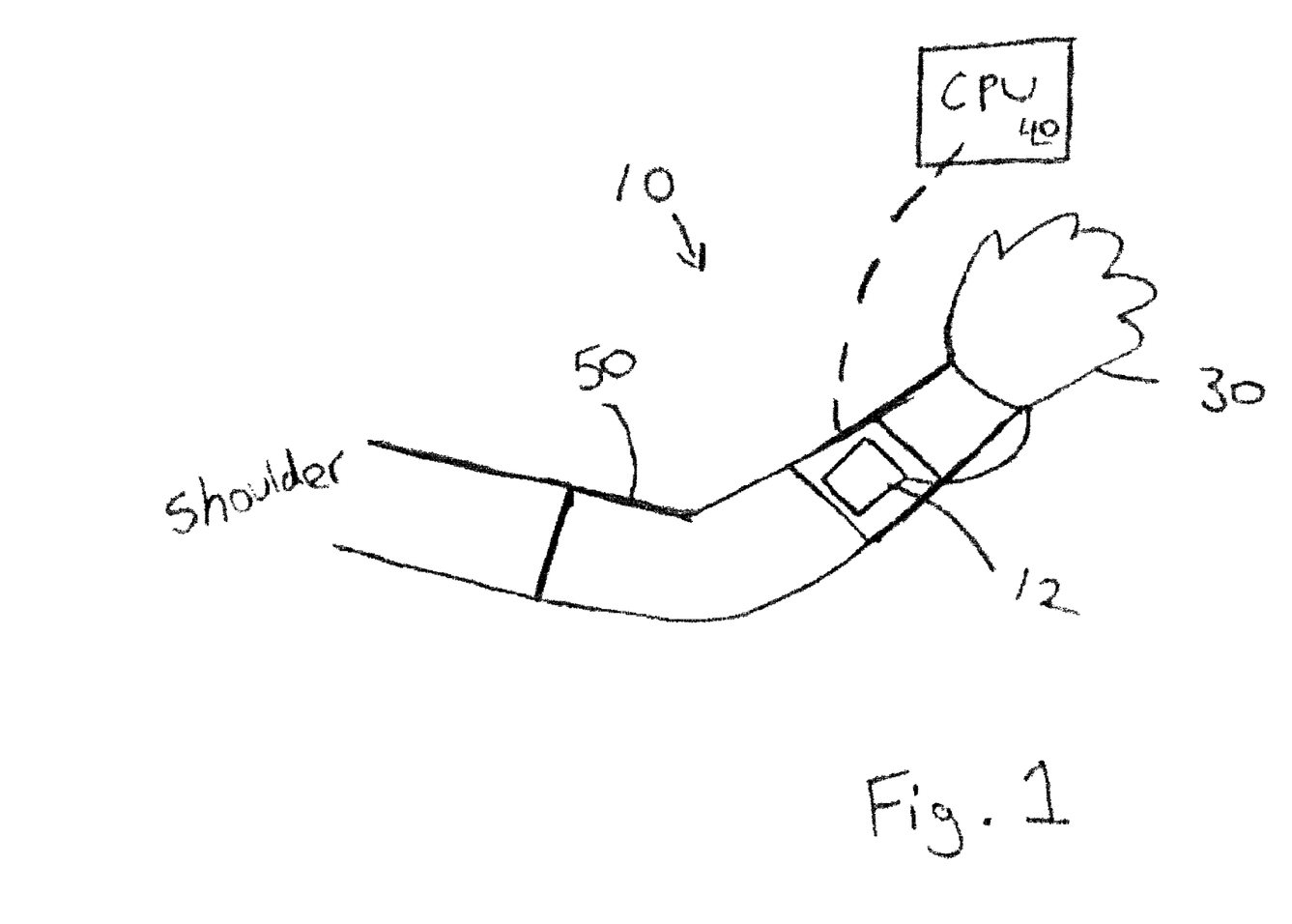
FIG. 1 shows an exemplary motion capture device according to one embodiment.

In one arrangement of the present invention, as shown in FIG. 1, a device 10 is provided for determining human limb position for, but not limited to, virtual and augmented reality, motion capture for animation, gaming, interactive media, medical, military, and general user-interface applications. In the arrangement described, device 10 is for motion capture associated with a limb having two primary segments, typically an arm or leg. Multiple devices 10 may be used, one for each limb. However, for the purposes of illustration, only one device 10 is shown, in the below examples, for use in motion capture for the movements of a wearer's arm (as shown in FIG. 1).

As shown in FIG. 1, device 10 employs at least one sensor array 12, mounted on a limb segment. It is noted that additional sensor arrays 12 may be added to device 10 for additional accuracy. However, for the purposes of illustration, device 10 employs a single primary sensor array 12.

Figure 2:
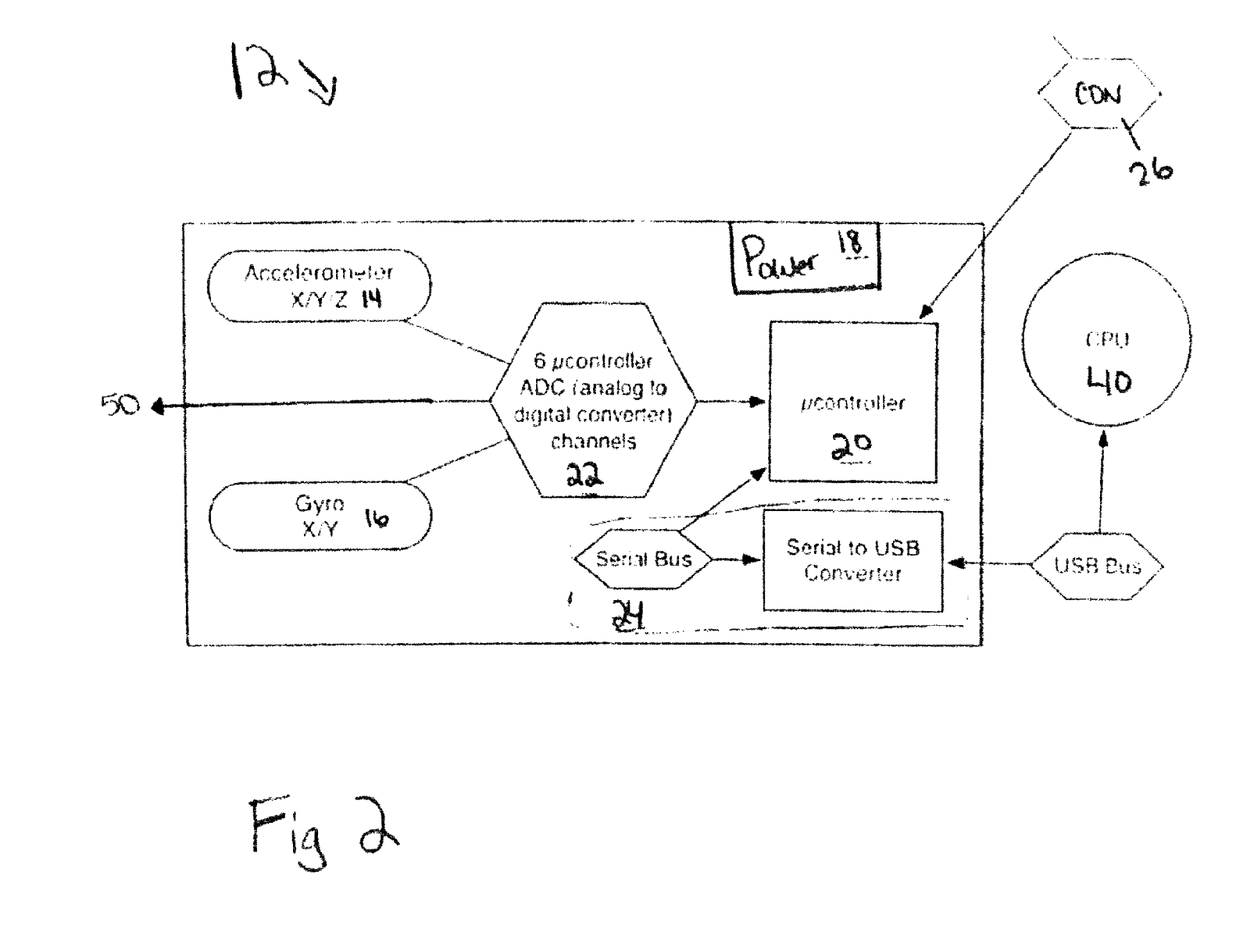
FIG. 2 shows a sensor array for the motion capture device of FIG. 1, in accordance with one embodiment.

As shown in FIG. 2, sensor array 12 includes a multi-axis accelerometer 14, and either a two- or three-axis gyroscopic sensor 16. Accelerometer 14 is preferably used to determine the orientation (pitch and roll) of the limb segment on which sensor array 12 has been positioned. Rotation of the limb segment, on which sensor array 12 is mounted, about the shoulder or pelvic joint, is determined by means of readings from sensors 14 and 50 as well as gyroscopic sensor 16.

In one arrangement, readings from gyroscopic sensor 16 and accelerometer 14 are preferably processed through a Kalman Filter for jitter-elimination by means of covariance matrix, and for automatic un-biasing of gyroscopic sensors 16. Basic averaging filters may also be used within device 12. A calibration routine may be included to provide for the un-biasing of gyroscopic sensors 16. As described below sensor 50 is intended to extend from sensor array 12 out over the flexible joint to the adjacent limb section. This flexible sensor may be a typical flex sensor, rotary potentiometer or other form of sensor that is capable of measuring the flex of bendable joint.

Figure 3:
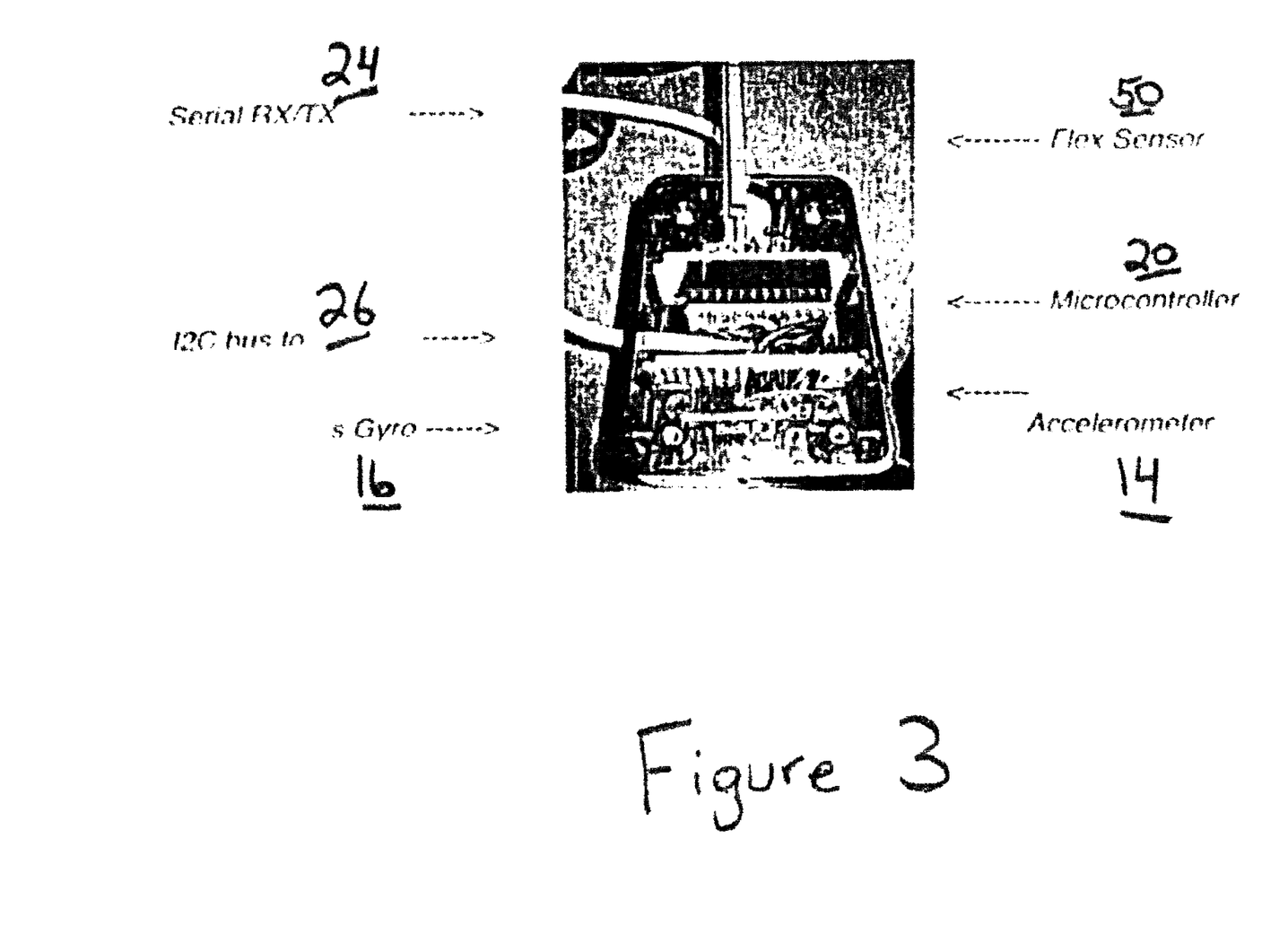
FIG. 3 is an illustration of the components off the sensor array of FIG. 2 in accordance with one embodiment.

In one arrangement, as shown in FIG. 2, an integrated or external power source 18 may be included within sensor array 12 for powering the various components. Also provided within sensor array 12 are programmable micro-controller or fixed-logic processor 20, analog-to-digital signal converter(s) 22, wired or wireless means of data relay to a CPU 40, such as external bus port/serial bus/USB converter 24. In one arrangement, an additional wired or wireless means of connecting other sensors or devices, such as I2C bus 26 or other connection format, may be included for relaying data stream or for interaction with sensor array 12. FIG. 3 shows an illustration of the relative positions of internal components of sensor array 12. Ideally, all of the components, of sensor array 12 are housed within a single structure, with the exception of flexible sensor 50.

Figure 4:
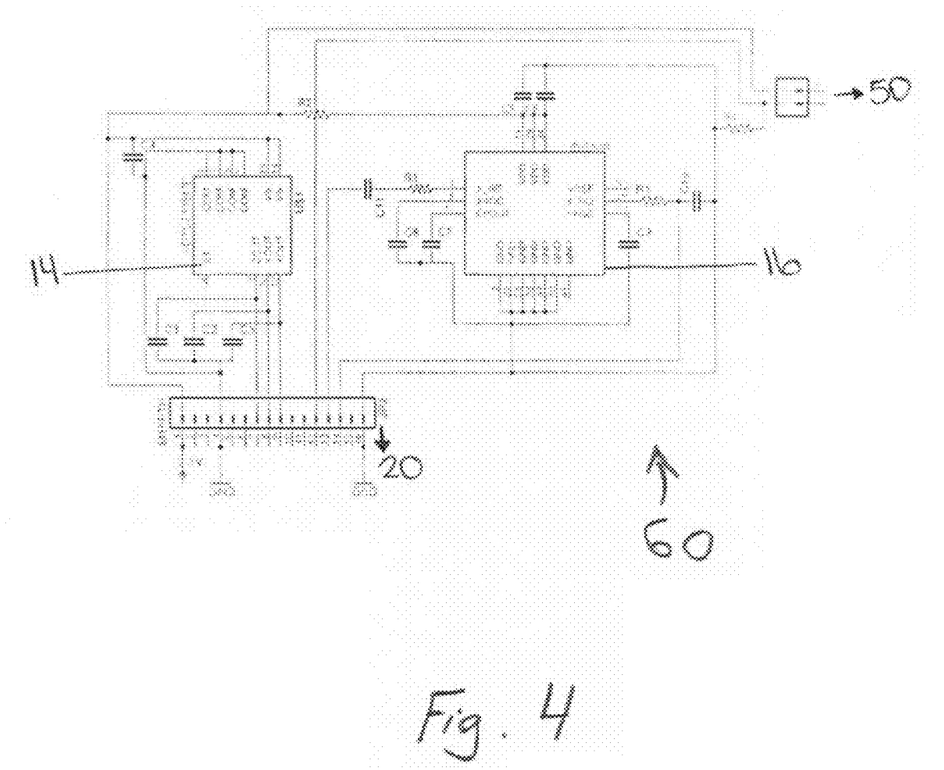
FIG. 4 is a printed circuit diagram of the sensor array of FIG. 2, in accordance with one embodiment.

In one arrangement as show in FIG. 4, device 10 may be implemented into a single circuit board 60. The labeled items in circuit diagram FIG. 5 relate to the components of sensor array 12 as shown in FIG. 12.

In one arrangement, printed circuit 60 may employ an optional integrated means of wireless communication such as ZigBee wireless module with the chipset(s), antenna, and battery necessary for its implementation. Such an arrangement would allow wireless communication of the sensor signals from accelerometer 14, gyroscopic sensor 16 and sensor 50.

Figure 5:
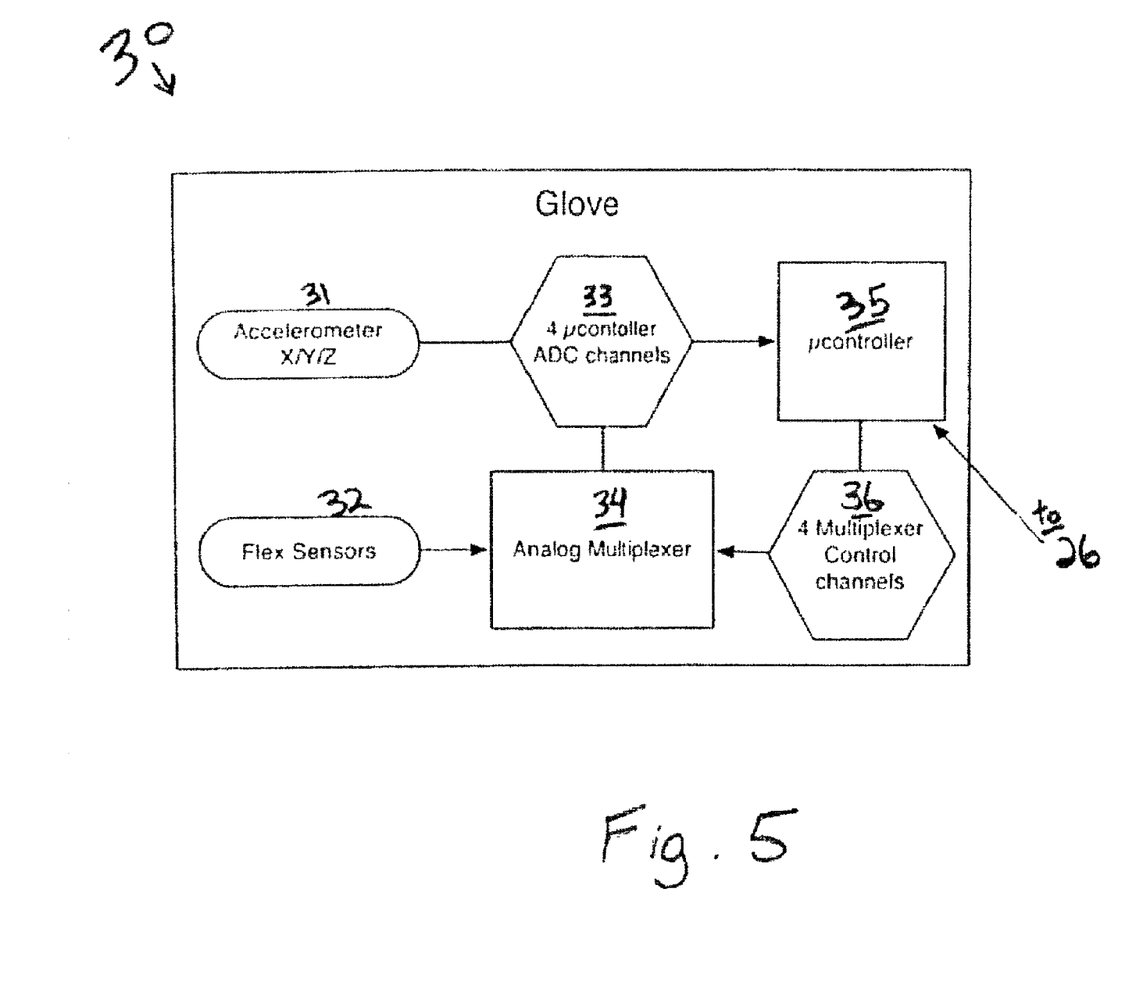
FIG. 5, shows a glove sensor coupled to the sensor array of FIGS. 1 and 2, in accordance with one embodiment.

In one arrangement, as shown in FIGS. 1 and 5, a glove 30 may be connected to I2C bus 26 of sensor array 12 in order to further include finger movements to augment the motion capture data collected by device 10. As illustrated in FIG. 3, glove 30 may employ the typical glove motion capture components of an accelerometer 31, flex sensors 32, analog-digital channels 33, analog multiplexer 34, controller 35 and multiplexer-control channels 36.

In one exemplary arrangement, as shown in FIG. 1, sensor array 12 is mounted on the upper or lower segment of a two-segment limb (shown mounted to lower segment), in proximity to the central joint of the limb. Extending from sensor array 12, one or more flex or stretch sensors 50 may extend from array 12 over the adjacent bending joint on the limb and onto at least a portion of the adjacent limb section.

Flexible or stretch sensor(s) 50 is(are) oriented across the central joint of the limb such that it measures the angle of flex of said joint. In one arrangement, the flexible/stretch sensor(s) 50 may employ an averaging filter to reduce signal noise ensure that.

Both sensor array 12 and flexible sensor 50 may be worn or mounted by any number of means, including through integration into a garment, Velcro™ straps or a brace-like sleeve or cuff to be worn around the joint.

Turning to the mathematical computation of limb position, utilizing the device 10 as set forth above, the calculation may be done either by onboard microcontroller 20, or the sensor values (from sensors 14, 16 and 50) may be returned by means of the relay 24 to computer 40 or other device where those calculations are made. In one arrangement, the limb position calculations may be made by a combination of both microcontroller 20 and external computer 40.

For the purposes of the following discussion regarding limb position calculation, references to the limb segment directly jointed to the users body center are referred to as "Segment A" (or upper arm segment), and that jointed to said Segment A and the hand or foot as "Segment B" (or lower arm segment).

In accordance with one embodiment, many different formulations may be used for determining limb position using the combined sensors 14, 16 and 50 readings described above.

In a first formula the limb position is determined by several steps:
1. Assuming that the hand is positioned directly in front of the shoulder, determine length and angle of a line drawn directly from the hand to the shoulder.
2. Using the tilt of the limb segment (sensor array 12 positioned on Segment B) measured on the axis perpendicular to the axial plane of limb flex, determine rotation of elbow about the line described in Step 1.
3. Accounting for the lateral rotation of Segment B about the joint, cumulatively determine rotation of limb about shoulder using lateral component of combined gyro axis readings as determined using the tilt measured in Step 2.

By the above described calculation steps device 10 is able to determine the lateral circular paths (diameter and relative vertical position), about the shoulder joint, on which the elbow and hand are located, and their rotational position on these paths. In the implementation of this formula, it may be assumed that the limb segments are of approximately equal length, though the formula can be adjusted to account for deviations.

According to the above arrangement, device 10 by the inclusion of a sensor(s) for the measurement of joint flex for tracking of limb position, half of the inertial sensors otherwise needed are eliminated. By this arrangement, only one primary sensor array 12 is required for tracking both segments of the limb and the spatial positioning of the hand or foot relative to the point at which the limb Segment A is joined to the body.

Thus, motion capture device 10 described above provides for the determination and tracking of human limb position with its functional components connected to, or mounted on, one or more printed circuit boards in sensor array 12.

Data interpretation, display, and rendering software on a computer, including custom mathematical methods may be used for the determination of limb positions from the values read from sensors 14, 16 and 50 as described above.

In another embodiment, a method for the interpretation of the data collected by the sensing device 10 is employed where the 3D coordinates of the central joint and the wrist or ankle joint, relative to the joint connecting the limb to the body, is derived.

The following is an exemplary summary of the use of the data from accelerometer 14, gyroscopic sensor 16 and flex sensor 50 for determining arm positioning and movement.

In this exemplary method, it is assumed that the z-axis of accelerometer 14 is parallel to the length of the forearm (segment B lower arm), that the y-axis is parallel to the axis of flex of the elbow, and the x-axis is perpendicular to the z- and y-axes. Another assumption is that the length of the upper-arm and the length of the forearm are approximately equal lengths A. The reading from flexible sensor 50 across the elbow gives us its angle of flex θ.

The accelerometer axis are read and interpreted as tilt values using the standard formula:

$$xTilt = a\tan 2(x, sqrt(y*y+z*z));$$

$$yTilt = a\tan 2(y, sqrt(x*x+z*z));$$

$$zTilt = a\tan 2(z, sqrt(y*y+x*x));$$

Figure 6:
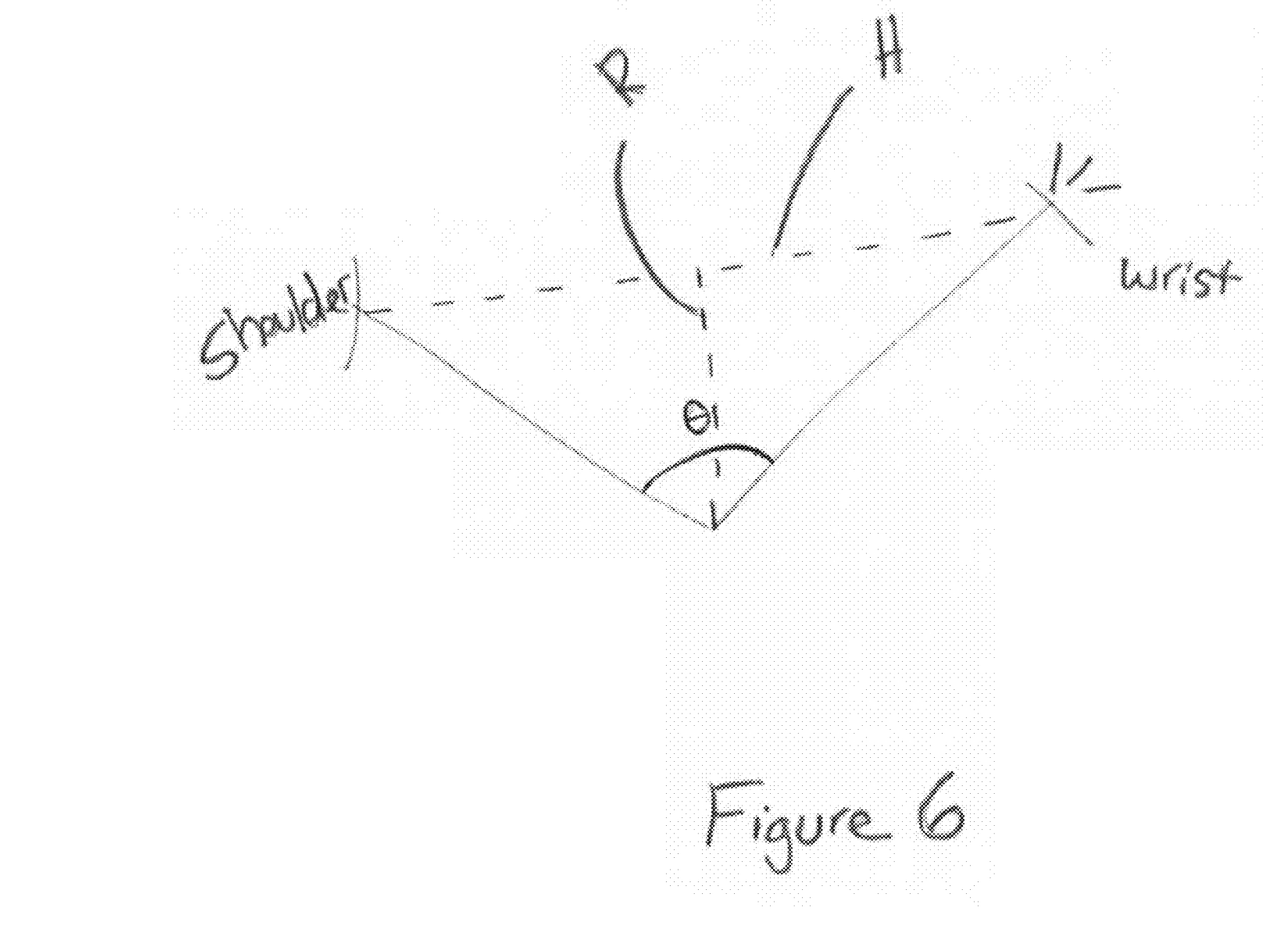
FIG. 6 illustrates a drawing showing the relevant measurements/calculations for determining position and movement in two dimensions, in accordance with one embodiment.

As shown in FIG. 6, the length of a line H drawn between the shoulder and the wrist is equal to:

$$2(\sin(\theta/2) \times A$$

The distance R from the elbow to the line H is equal to:

$$\cos(\theta/2) \times A$$

Thus, an angle psi of a line can be determined, relative to the horizontal plane, drawn between the shoulder and the wrist, by the following formula:

$$zTilt - a\tan((\cos(yTilt) \times \cos(\theta/2)*A)/(\sin(\theta/2) \times A))$$

The distance F from the elbow to a horizontal plane rotated around the axis perpendicular to the line drawn between the shoulder and wrist, so as to lay parallel to this line, is equal to:

$$\cos(yTilt) \times R$$

The distance V from the shoulder to the hand, on the y-z plane of the environment (disregarding lateral displacement along the x-axis) is equal to:

$$\sqrt{(F2+0.5H2)}$$

Therefore:

$$elbowX = \cos(psi - a\tan(V/0.5H)) \times V$$

$$elbowY = \sin(psi - a\tan(V/0.5H)) \times V$$

$$elbowZ = \sin(yTilt) \times R$$

Such measurements may be used to find the location of limb, for example with in a two dimensional plane.

In one arrangement this may be coded as:

$$h = (\sin(0.5*elbowAngle)*forearmLength);$$

$$r = (\cos(0.5*elbowAngle)*forearmLength);$$

$$zFF = \cos(HALF\_PI + yTilt)*r;$$

$$angle = (PI + zTilt) - (a\tan(zFF/h));$$

$$hx = -(\cos(angle)*2*h);$$

The y-axis in the coding environment is inverted, with positive values descending from shoulder level.

$$hy = \sin(angle)*2*h;$$

$$f = sqrt(sq(zFF) + sq(h));$$

$$ex = \cos(zTilt - (2*(a\tan(zFF/h))))*f;$$

$$ey = \sin(angle - (a\tan(zFF/h)))*f;$$

$$ez = (\sin(HALF\_PI + yTilt)*-r);$$

This calculation returns wrist position hx/hy and elbow position ex/ey/ez.

Thus the above arrangement utilizes the accelerometer 14 and flexible sensor 50 to begin the initial three dimensional calculations.

Figure 7:
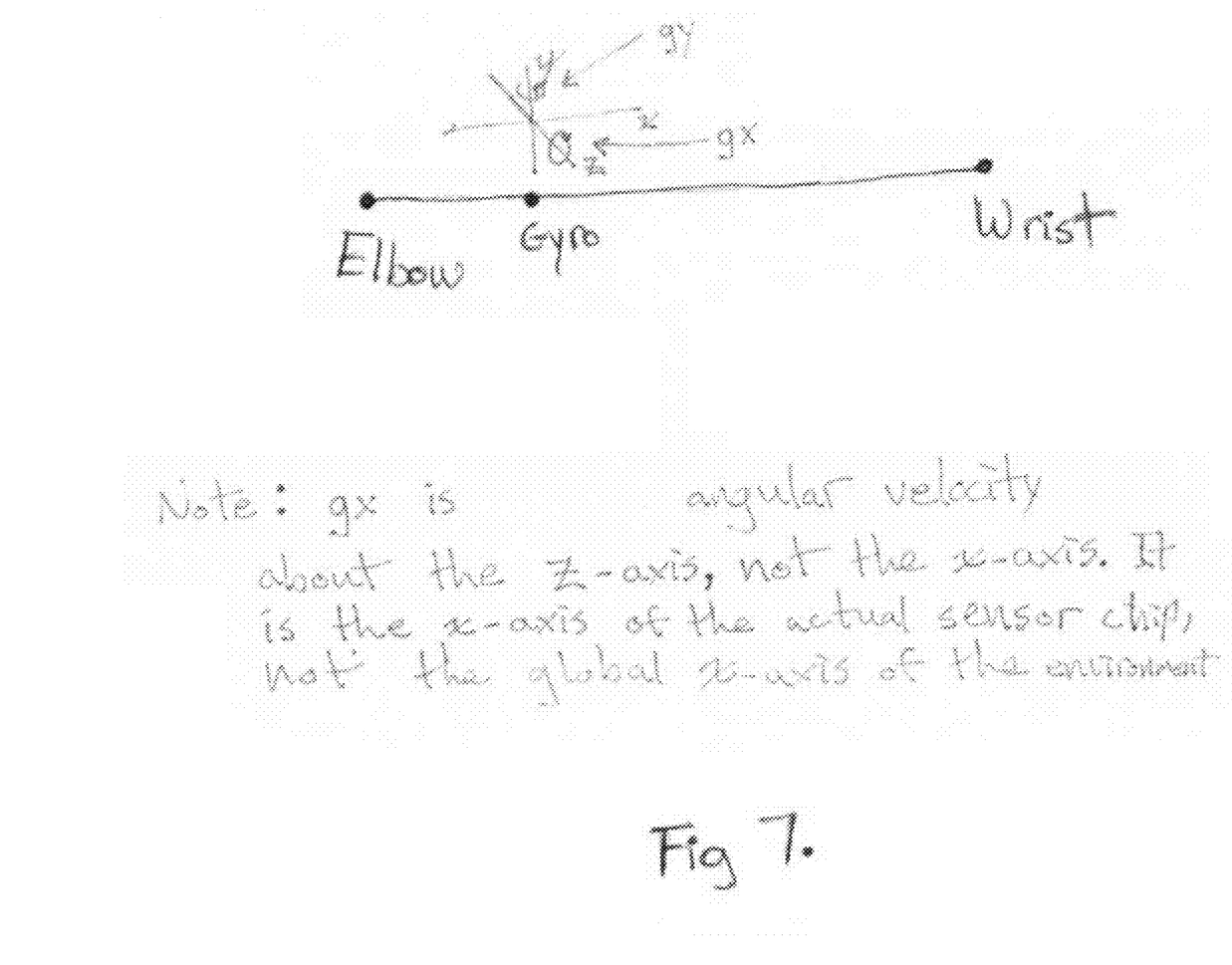
FIG. 7 illustrates a drawing showing the relevant measurements/calculations for determining position and movement in three dimensions, in accordance with one embodiment.

Once the two dimensional is determined as above, the three dimensional aspect may be calculated using such data from the accelerometer (X, Y, Z tilt) and from the flex sensor (θ), supplemented by gyroscopic data input in at least the 2 dimensions perpendicular to the length of the forearm member.

$$gx = radians(map(gxRaw, gxZero, gxZero+gyroScaleX, 0, 90));$$

$$gy = radians(map(gyRaw, gyZero, gyZero+gyroScaleY, 0, 90));$$

For example, In the above code, raw sensor input is remapped from the range defined by the gyro sensor 16 calibrated to zero (ie. the voltage it returns when there is no angular velocity across that axis) and gyro's scale factor (ie. the voltage that the gyro returns when rotating approximately 90°/second about that axis) to the range between 0°/second and 90°/second, and then converting it to radians.

In another arrangement, the measurements could be directly converted to radians. The map( ) function also projects outside of the specified range so that, for instance, a gxRaw of gxZero+2*gyroScaleX results in a value of 180°/second.

These additional inputs may be used in conjunction with the other measurements as follows:

$$gxGy = sqrt(sg(gx) + sg(gy)) // The\ compound\ vector\ defined\ by\ gx\ and\ gy$$

$$if(gx <= 0)$$

$$gxGyTheta = TWO\_PI - a\cos(gy/gxGy);$$

else $$gxGyTheta = a\cos(gy/gxGy);$$

In this arrangement, the above conditional prevents the use of a negative angle when computing gxGyTheta. gxGyTheta is the angle, relative to the gx axis of measurement Where Rotation about the shoulder+=(cos(gxGyTheta−yTilt)* gxGy)*(((float)timeDelta)/1000);

Here, the magnitude of the lateral component of gxGy, which is the cosine of the compound vector, gxGy, is calculated and multiplied by the difference between gxGyTheta and the yTilt value derived from the accelerometer 14 data.

That calculation is then multiplied by the time elapsed between readings (converted from milliseconds to seconds by converting the timeDelta, which is an integer value in milliseconds, to a floating-point number and dividing it by 1000) to arrive at the value that should be added or subtracted to the cumulative rotation of the total arm assembly about the shoulder.

While only certain features of the invention have been illustrated and described herein, many modifications, substitutions, changes or equivalents will now occur to those skilled in the art. It is therefore, to be understood that this application is intended to cover all such modifications and changes that fall within the true spirit of the invention.

What is claimed is:

1. A motion capture device, for capturing motion of an arm having two sections, connected by an elbow joint, said device comprising:
    a sensor array mounted to a first section of an arm, said sensor array having at least one gyroscopic sensor element and at least one accelerometer; and
    a sensor for attachment across the elbow joint, coupled to said sensor array and extending away from said sensor array across said elbow joint to a second section of said arm, wherein a combination of data obtained from said at least one gyroscopic sensor element and at least one accelerometer of said sensor array and said sensor for said elbow joint are configured to determine the location and motion of the arm including the lateral circular paths (diameter and relative vertical position), about a shoulder joint of said arm, on which said elbow joint and a corresponding hand are located, and their rotational position on these paths,
    such device being further configured to;
    i) determine the length and angle of a line drawn directly from the hand to the shoulder, assuming that the hand is positioned directly in front of the shoulder,
    ii) determine rotation of said elbow joint about said line drawn directly from the hand to the shoulder using the tilt of the arm segment measured on the axis perpendicular to the axial plane of arm flex; and
    iii) cumulatively determine lateral rotation of the arm about said shoulder joint using said lateral circular paths from said combination of data obtained from said at least one gyroscopic sensor element and at least one accelerometer of said sensor array.

2. The motion capture device as claimed in claim 1, further comprising a plurality of sensor arrays on said first section of said arm.

3. The motion capture device as claimed in claim 1, wherein said accelerometer is a multi-axis accelerometer.

4. The motion capture device as claimed in claim 3, wherein said accelerometer is used to determine the orientation (pitch and roll) of the arm segment on which said sensor array is positioned.

5. The motion capture device as claimed in claim 1, wherein said gyroscopic sensor element is selected from the group consisting of a two- or three-axis gyroscopic sensors.

6. The motion capture device as claimed in claim 1, wherein readings from said gyroscopic sensor and said accelerometer are processed through a Kalman Filter for jitter-elimination by means of covariance matrix, and for automatic un-biasing of said gyroscopic sensor.

7. The motion capture device as claimed in claim 1, wherein said sensor for attachment across the elbow joint is selected from the group consisting of flex sensors, rotary potentiometers or other sensors capable of measuring the flex of said elbow joint.

8. The motion capture device as claimed in claim 1, wherein said sensor array is implemented into a single circuit board.

9. The motion capture device as claimed in claim 8, wherein said circuit board employs an integrated means of wireless communication for wireless communication between said device and a host computer.

10. The motion capture device as claimed in claim 1, further comprising a glove connected to said sensor array in order to further include finger movements to augment the motion capture data collected by said device.

11. The motion capture device as claimed in claim 1, said device configured to interpret the data collected by said sensors of said device, where the 3D coordinates of the elbow joint and a wrist joint, relative to the shoulder joint connecting the arm to the body, is derived, according to accelerometer axis tilt values using the standard formula $$\text{xTilt} = a\tan 2(x, \text{sqrt}(y^*y + z^*z));$$

$$\text{yTilt} = a\tan 2(y, \text{sqrt}(x^*x + z^*z)); \text{ and}$$

$$\text{zTilt} = a\tan 2(z, \text{sqrt}(y^*y + x^*x))$$

assuming that the z-axis of accelerometer is parallel to the length of the forearm (segment B lower arm);
    assuming that the y-axis is parallel to the axis of flex of the elbow;
    assuming that the x-axis is perpendicular to the z- and y-axes;
    assuming that the length of the upper-arm and the length of the forearm are approximately equal lengths A; and
    assuming the reading from flexible sensor across the elbow gives us its angle of flex θ, wherein.

12. The motion capture device as claimed in claim 11, wherein said device is configured to derive the 3D coordinates of the elbow joint and the wrist joint, relative to the shoulder joint connecting the arm to the body, by calculating the length of a line H drawn between the shoulder and the wrist is equal to:

$$2(\sin(\theta/2) \times A$$

and, the distance R from the elbow to the line H is equal to:

$$\cos(\theta/2) \times A$$

wherein an angle psi of a line is determined, relative to the horizontal plane, drawn between the shoulder and the wrist, by the following formula:

$$\text{zTilt} - a\tan((\cos(\text{yTilt}) \times \cos(\theta/2)^* A)/(\sin(\theta/2) \times A)).$$

13. The motion capture device as claimed in claim 12, wherein said device is configured to deriving the 3D coordinates of the elbow joint and the wrist joint, relative to the shoulder joint connecting the limb to the body
    by calculating that the distance F from the elbow to a horizontal plane rotated around the axis perpendicular to said line drawn between the shoulder and wrist, so as to lay parallel to this line, is equal to:

$$\cos(\text{yTilt}) \times R; \text{ and}$$

by calculating that the distance V from the shoulder to the hand, on the y-z plane of the environment (disregarding lateral displacement along the x-axis) is equal to:

$$\sqrt{(F2 + 0.5H2)}$$

such that $$\text{elbowX} = \cos(\text{psi} - a\tan(V/0.5H)) \times V$$

$$\text{elbowY} = \sin(\text{psi} - a\tan(V/0.5H)) \times V$$

$$\text{elbowZ} = \sin(\text{yTilt}) \times R$$

so as to determine the location of limb, within a two dimensional plane.

14. The motion capture device as claimed in claim 13, wherein wherein said device is configured to derive the 3 D coordinates of the elbow joint and the wrist joint, relative to the shoulder joint connecting the limb to the body by using data from the accelerometer (X, Y, Z tilt) and from the flex sensor (θ), supplemented by gyroscopic data input in at least the two dimensions perpendicular to the length of the forearm member, where gx=radians(map(gxRaw,gxZero,gxZero+gyroScaleX, 0,90));

and gy=radians(map(gyRaw,gyZero,gyZero+gyroScaleY,0,90)).

15. A motion capture device, for capturing motion of a leg having two sections, connected by a knee joint, said device comprising:
   a sensor array mounted to a first section of a leg, said sensor array having at least one gyroscopic sensor element and at least one accelerometer; and
   a sensor for attachment across the knee joint, coupled to said sensor array and extending away from said sensor array across said knee joint to a second section of said leg, wherein a combination of data obtained from said at least one gyroscopic sensor element and at least one accelerometer of said sensor array and said sensor for said knee joint are configured to determine the location and motion of the leg including the lateral circular paths (diameter and relative vertical position), about a hip joint of the leg, on which said knee joint and a corresponding foot are located, and their rotational position on these paths,
such device being further configured to;
i) determine the length and angle of a line drawn directly from the foot to the hip join, assuming that the foot is positioned directly in front of the hip,
ii) determine rotation of said elbow joint about said line drawn directly from the foot to the hip using the tilt of the leg segment measured on the axis perpendicular to the axial plane of leg flex; and
iii) cumulatively determine lateral rotation of the leg about said hip joint using said lateral circular paths from said combination of data obtained from said at least one gyroscopic sensor element and at least one accelerometer of said sensor array.

* * * * *